(12) United States Patent
Park et al.

(10) Patent No.: US 8,624,180 B2
(45) Date of Patent: Jan. 7, 2014

(54) RESOLUTION ENHANCEMENT FOR ION MOBILITY SPECTROMETERS

(75) Inventors: Melvin Andrew Park, Billerica, MA (US); Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 177 days.

(21) Appl. No.: 13/094,146

(22) Filed: Apr. 26, 2011

(65) Prior Publication Data

US 2012/0273674 A1 Nov. 1, 2012

(51) Int. Cl.
*H01J 49/00* (2006.01)

(52) U.S. Cl.
USPC ........... 250/287; 250/281; 250/282; 250/288; 250/396 R; 250/397

(58) Field of Classification Search
USPC ................. 250/281, 282, 286, 289, 290, 294, 250/396 R, 397, 398, 396 ML, 288, 287
See application file for complete search history.

(56) References Cited

U.S. PATENT DOCUMENTS

| | | | |
|---|---|---|---|
| 7,514,676 B1 | 4/2009 | Page | |
| 7,838,826 B1 | 11/2010 | Park | |
| 2010/0090102 A1 | 4/2010 | Rather | |
| 2010/0327157 A1* | 12/2010 | Green et al. | 250/282 |
| 2011/0062322 A1 | 3/2011 | Franzen | |

FOREIGN PATENT DOCUMENTS

GB 2419462 A 4/2006

OTHER PUBLICATIONS

British Search Report Dated Aug. 28, 2012.

* cited by examiner

*Primary Examiner* — Jack Berman
*Assistant Examiner* — Hanway Chang
(74) *Attorney, Agent, or Firm* — ROBIC, LLP

(57) ABSTRACT

In an ion mobility spectrometer in which a gas pushes ions along a spectrometer axis against and over an electrical field barrier, the electric field barrier is generated with a plateau of slightly increasing height along the axis of the spectrometer. Alternately, the electric filed barrier may have a plateau with constant height, but the gas flow decreases in velocity along the axis of the spectrometer in the vicinity of the plateau.

11 Claims, 2 Drawing Sheets

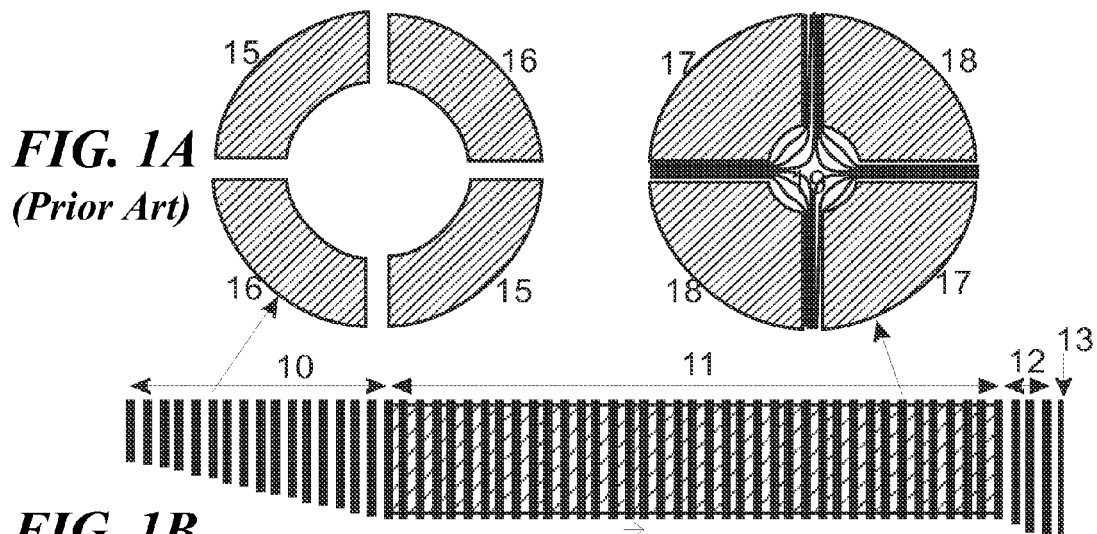
FIG. 1A (Prior Art)
FIG. 1B (Prior Art)
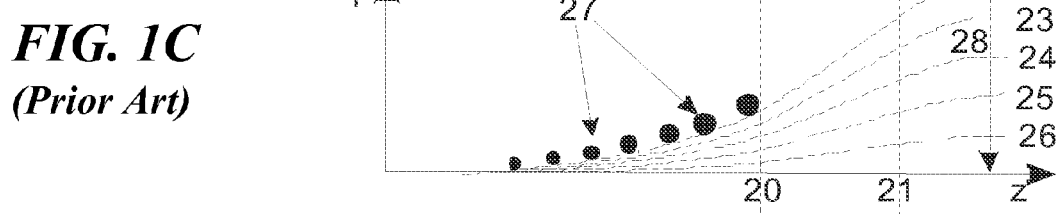
FIG. 1C (Prior Art)
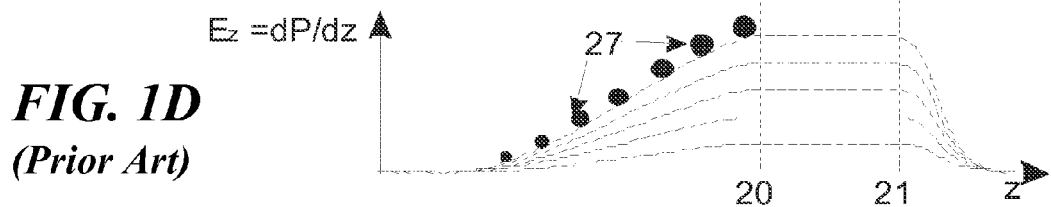
FIG. 1D (Prior Art)

RESOLUTION ENHANCEMENT FOR ION MOBILITY SPECTROMETERS

BACKGROUND

The invention relates to devices and methods for the acquisition of ion mobility spectra in ion mobility spectrometers which apply gas flows to push trapped ions over electric field barriers. Mass spectrometers can only ever determine the ratio of the ion mass to the charge of the ion. Where the terms "mass of an ion" or "ion mass" are used below for simplification, they always refer to the ratio of the mass m to the dimensionless number of elementary charges z of the ion. This charge-related mass m/z has the physical dimension of a mass; it is often also called "mass-to-charge ratio", although this is dimensionally incorrect. "Ion species" shall denote ions having the same elemental composition, the same charge and the same three-dimensional structure. Ion species generally comprise all the ions of an isotope group, which consist of ions of slightly different masses.

Different kinds of isomers are known for bioorganic molecules: isomers related to the primary structure (structural isomers) and isomers related to the secondary or tertiary structure (conformational isomers). These isomers have different geometrical forms but exactly the same mass. It is therefore impossible to differentiate between them on the basis of their mass. Some information as to the structure can be obtained from fragment ion mass spectra; however, an efficient and certain way to recognize and distinguish such isomers is to separate their ions according to their different ion mobilities.

Nowadays, the mobility of ions is often measured via their drift velocities through stationary gases under the influence of an electric field. Long drift tubes are filled with an inert, stationary gas (such as helium, nitrogen or argon). The ions of the substance under investigation are pulled through the gas by means of an homogeneous electric field, which is produced by suitable DC potentials applied to ring electrodes arranged along the drift region. The friction with the gas results in a constant drift velocity $v_d$ for each ion species which is proportional to the electric field strength E: $v_d = \mu \times E$. The proportionality factor $\mu$ is called the "ion mobility" of the ion species. The ion mobility $\mu$ is a function of the gas temperature, gas pressure, type of gas, ion charge and, in particular, the collision cross-section of the ions.

The ion mobility resolving power ("mobility resolution" for short) is defined as dimensionless numbers $R_{mob} = \mu/\Delta\mu$, where $\Delta\mu$ is the width of the ion signal of the mobility $\mu$ at half height, measured in units of ion mobility. Compared to the numerical values for similarly defined mass resolutions in high resolution mass spectrometers, amounting usually to many ten thousands, the ion mobility resolutions which can be achieved in practice are generally very low. The first commercial combination of ion mobility spectrometer and mass spectrometer for bioorganic ions has a maximum mobility resolution of only $R_{mob}=40$. With a mobility resolution of $R_{mob}=40$, two ion species whose collision cross-sections differ by only five percent can be separated very well. Only highly specialized groups of scientists have, as yet, been able to achieve significantly higher mobility resolutions than $R_{mob}=100$, in rare individual cases up to $R_{mob}=200$, making it possible to differentiate between ion species whose mobilities differ by only one to two percent. Ion mobility spectrometers with a resolution above $R_{mob}=100$ shall be called "high resolution" here.

High-resolution time-of-flight mass spectrometers with orthogonal injection of the ions (OTOF-MS), in particular, have proven successful for combinations of mobility spectrometers with mass spectrometers. For such combinations, the high-resolution ion mobility spectrometers of the ion drift type have the disadvantage of being several meters long. Such a solution is unfavorable for instruments marketed commercially. Even ion mobility spectrometers with a straight drift region offering only moderate resolution are about one meter long. For the construction of small, high-resolution mobility analyzers, one therefore has to look for a solution which shortens the overall length but does not diminish the mobility resolution.

In document U.S. Pat. No. 7,838,826 B1 (M. A. Park, 2008), an ion mobility spectrometer is presented as newest state of the art, the size of which amounts to about ten centimeters only. It is based upon the well-known effect of moving gases blowing ions against and over an electric counter-field barrier instead of pulling ions through a stationary gas. The instrument of M. A. Park is designed into a modified ion funnel built into a commercial time-of-flight mass spectrometer. Unlike many other trials to build small ion mobility spectrometers, the device by M. A. Park has already achieved ion mobility resolutions in excess of $R_{mob}=100$, exhibiting high mobility resolution.

The apparatus of M. A. Park and its operation are schematically illustrated in FIGS. 1A to 1D. FIG. 1B shows, how the parts (10) and (12) of a quadrupolar funnel, open as usual to the flow of gas between the electrodes, are separated by a closed quadrupole device (11), vertically sliced into thin electrodes (17, 18) forming a circular tube arranged around the z-axis of the device. The electrode slices are separated by insulating material closing the gaps between the electrodes around the tube. FIG. 1A shows the shape of the electrodes of the funnel (15, 16) in a direction normal to the z-axis and the shape of the electrodes in a direction normal to the z-axis that form the quadrupole tube (17, 18), the latter with equipotential lines of the radially quadrupolar RF field inside the tube at a given time. A differential pumping system of a mass spectrometer (not shown) surrounds the ion mobility spectrometer and is dimensioned to cause a gas to flow, at pressures between several tens to hundreds of pascals, constantly through the tube (11) in a laminar way, thereby causing the gas flow to assume the usual parabolic velocity profile (14). Ions entering the first funnel (10) entrained in a gas, are focused onto the axis of the tube (11) by the pseudopotential forces of the quadrupolar RF field and move, driven by the gas, along the axis of the tube towards its exit through the apertured diaphragm (13). Most of the gas escapes through gaps between the electrodes of the funnel part (12).

An ion funnel (10) or (12) usually is operated with apertured diaphragms the openings of which taper to smaller diameters thus forming an inner volume in the shape of a funnel. Two phases of an RF voltage are applied alternately to the diaphragms to build up a pseudopotential which keeps the ions away from the funnel walls. The ion funnel entrance part (10) and exit part (12) are here built from electrodes which are divided into four parts to allow a more complicated RF field to be applied, but this is not essential for the operation of this ion mobility spectrometer.

FIGS. 1C and 1D show, in two diagrams, different DC potential profiles P (22) to (26) along the z-axis, and corresponding barriers of the electric counter field $E_z = dP/dz$, respectively. The potential profiles are produced by a network of precisely chosen resistors between the electrode slices, operating as voltage dividers. In this way, only a single voltage has to be applied and forms the complete profile; changing this voltage changes the potential profiles (22 to 26) and change the height of the electric barriers as a whole.

The operation of the ion mobility spectrometer will be described by the sequence in which the potential profiles are changed. The operation starts with a filling process. The steepest potential profile (22) is generated by a voltage in the order of 100 to 200 volt, producing the highest electric field barrier. The ions (27) are blown by the gas flow against the field barrier and are stopped there because they cannot surmount the field barrier. Ions with high mobility gather at the foot of the barrier, ions with high collision cross section (low mobility) gather near the summit, as symbolically indicated by the size of the ion dots (27). When a suitable number of ions have been collected, further ions are prevented from entering the ion mobility spectrometer, e.g., by reversing the DC potential gradient in the ion funnel (10). In order to acquire a spectrum, the potential profile (22) is smoothly lowered by decreasing the voltage continuously in a procedure denominated a "scan" (28), through profile states (23) to (26). During the scan, ions of higher and higher mobilities can surmount the decreasing summit of the barrier and exit the ion mobility spectrometer. They are measured by an ion detector, favorably by a mass spectrometer. The measured ion current curve presents directly the ion mobility spectrum from low ion mobilities to high ion mobilities. This device is denominated a "TIMS", or "trapped ion mobility spectrometer".

A characteristic feature of this instrument is the long increasing part of the electric field barrier until position (20), the start of the plateau as shown in FIG. 1D. This long ascent between foot and top of the barrier collects the ions (27) in a rather large volume along the z-axis, reducing greatly any space charge effects.

Another characteristic feature of this instrument is the flat plateau of the height of the electric field barrier between positions (20) and (21) on the z-axis, also shown in FIG. 1D. If the barrier is lowered slowly during an acquisition, ions have to dwell, for about a millisecond while passing the flat plateau, in a critical balance between the pushing force of the hundreds of gas collisions and the retarding force of the electric counter field, before they are finally blown from the end of the plateau into weaker field regions. In this millisecond, a high number of gas collisions causes a statistically equal selection of all ions of the same mobility, resulting in the high mobility resolution.

With this instrument, the ion mobility resolution $R_{mob}$ was found to increase with decreasing acquisition speed. Ion mobilities in excess of $R_{mob}$=100 have been achieved with the small apparatus in first experiments, but only by very slow scanning, allowing only for low repetition rates of the instrument's spectrum acquisition. Furthermore, with extremely slow acquisition speeds, the noise in the ion current peaks for ions of one mobility are drastically increased, because there are generally only a few ions per peak, and these ions are distributed over a longer period of time, resulting in a torn structure of the peak.

It should be mentioned here, that there are other types of short ion mobility spectrometers using gas flows. Document US 2010/0,090,102 A1 (O. Raether et al, 2008) describes, how a freely expanding gas flow from a small opening can be used to drive entrained ions over an electrical barrier within an ion funnel without quadrupolar RF field. In document GB 2473723 A (J. Franzen, 2009), an apparatus is presented which generates a supersonic gas flow by a Laval nozzle, the supersonic gas flow driving entrained ions over an electrical barrier. In this case, the supersonic gas flow with entrained ions is not enclosed by any radially confining field, particularly not by an RF multipole field.

SUMMARY

In accordance with the principles of the present invention, the electrical field barrier with a plateau as described in document U.S. Pat. No. 7,838,826 is modified in such a way that the height of the plateau increases slightly along the axis of the mobility spectrometer. If the plateau of the counter field barrier profile is no longer flat, but is modified to increase its height slightly with z, the highest mobility resolution can be achieved with moderately fast acquisition speeds. For each plateau gradient value, there exists an optimum of the acquisition speed for highest resolution.

The field barrier with the slightly increasing height of the plateau may be a DC electric field barrier or an RF pseudofield barrier, formed by a pseudopotential distribution.

In the instrument of M. A. Park, a DC electric field barrier with slightly increasing plateau height may be generated by slightly increasing resistances in the chain of resistors forming the voltage divider network.

The slightly increasing plateau generates equipotential surfaces vertically to the axis, which are no longer flat but slightly convex. As a result, the electric counter field is strongest in the axis and gets increasingly weaker outside the axis. Ions in the axis experience the strongest counter field, and ions a little outside the axis experience somewhat weaker counter fields. If the gas flow is laminar and shows a parabolic velocity profile, the slower gas flow outside the axis is compensated, in a first order, by the form of the electric counter field.

For an ion mobility spectrometer with this slightly increasing plateau, the optimum acquisition method decreases the field strength, E, of the electric barrier with $E_z(t)=c/t$ where c is a constant and t is time. This scan function not only generates ion mobility spectra with highest ion mobility resolution at moderate scan speed, but also generates a linear mobility scale.

BRIEF DESCRIPTION OF THE DRAWINGS

FIGS. 1A to 1D schematically illustrate the design and operation of an ion mobility spectrometer according to the state of the art, as described in U.S. Pat. No. 7,838,826 B1 (M. A. Park, 2008).

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

As mentioned above, the present invention is based on ion mobility spectrometers in which a gas is blowing the ions against and over an electric field barrier. As ion mobility spectrometer, one of the instruments as described in documents US 2010/0,090,102 A1 (O. Raether et al, 2008), GB 2473723 A (J. Franzen, 2009), and particularly U.S. Pat. No. 7,838,826 B1 (M. A. Park, 2008) may be used. The instrument of M. A. Park is schematically illustrated in FIGS. 1A to 1D. This instrument has produced ion mobility resolutions in excess of $R_{mob}$=100, but this resolution requires a drastically decreased acquisition speed, resulting in mobility spectra wherein the ion peaks are extremely noisy. A slow acquisition speed also decreases the spectrum acquisition rate, and thus the sensitivity of the method.

A first inventive embodiment includes a laminar gas flow with constant flow velocity and a counter field barrier profile with a plateau which increases its height slightly along the axis z. FIG. 2B exhibits such an electric barrier with slightly increasing plateau within a tube, the plateau positioned between z-positions (40) and (41). The highest mobility resolution will then be achieved with moderate instead of slowest acquisition speeds. The optimum acquisition speed for highest resolution depends on the gradient of the plateau. The resolution is the higher, the longer the cloud of ions of one mobility is kept in the exact balance of the driving friction force of the gas and the retarding electric field force while passing the summit of this barrier. During this process of passing the plateau, the voltage scan during the acquisition continues to decrease the height of the barrier, but due to the spatial gradient of the barrier's height, the ions are kept within this critical balance for one to three milliseconds, homogenizing the statistical Brownian movements of the ions caused by their Boltzmann energy distribution. The ions even may be less affected by space charge phenomena.

The optimum gradient of the electric barrier and the optimum length of the electric barrier have to be found by experiments or by mathematical simulations.

The electric field barrier may be a DC electric field barrier, as in the instrument of M. A. Park, or an RF pseudofield barrier, the latter being formed by a pseudopotential profile generated by RF voltages supplied to a suitable arrangement of electrodes.

The plateau of an electric DC field barrier with slightly increasing height may be generated by slightly increasing resistances in the chain of resistors forming the voltage divider network at a suitable arrangement of electrodes.

Figure 2A:
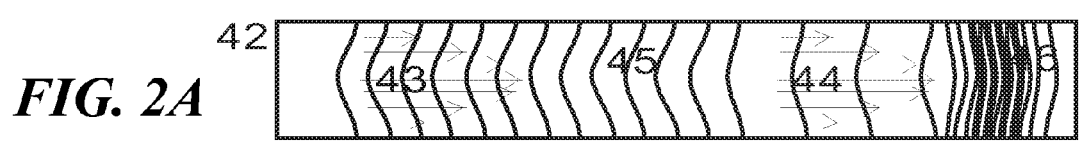
FIG. 2A shows the convex equipotential surfaces (55), (56) within a tube resulting from the field barrier of the present invention.
Figure 2B:
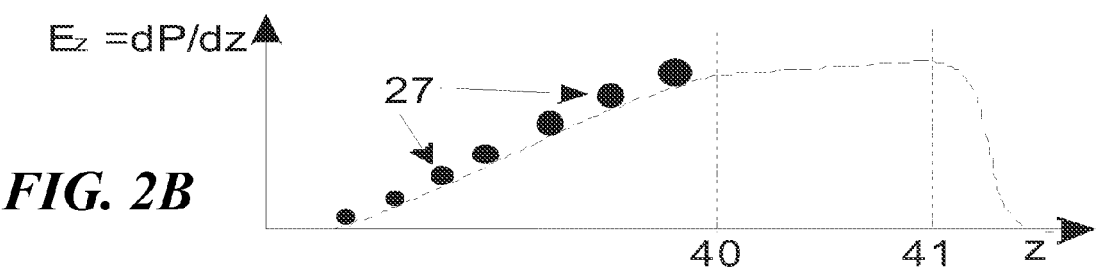
FIG. 2B schematically illustrates an electrical counter field barrier with a plateau the height of which increases slightly between z positions (40) and (41).

As shown in FIG. 2A, the slightly increasing plateau generates equipotential surfaces (45) and (46), which are no longer flat. In the front ascent of the barrier and on the plateau, the equipotential surfaces are convex towards the gas flow. As a result, the electric counter field is strongest in the axis and gets increasingly weaker outside the axis. Ions in the axis experience the strongest counter field, and ions a little outside the axis experience somewhat weaker counter fields. If correctly designed, this form of the electric field may compensate for the slower gas flow outside the axis by the parabolic velocity profile, at least in a first order.

Figure 3A:
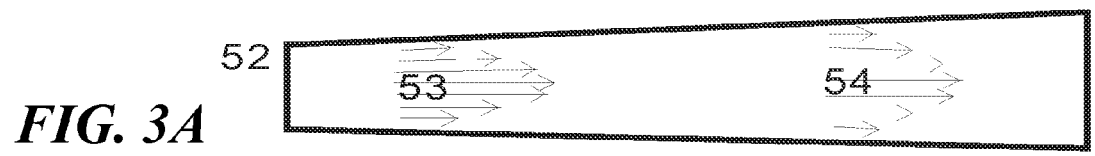
FIG. 3A illustrates schematically a tube with widening inner diameter, showing an decreasing gas flow velocity (53) to (54) within the tube of a mobility spectrometer.
Figure 3B:
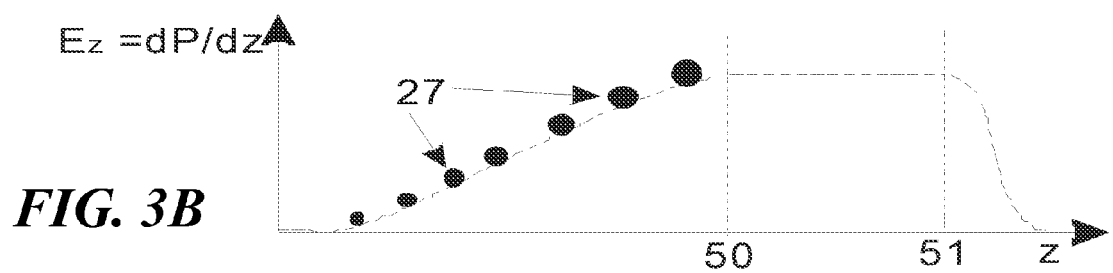
FIG. 3B schematically illustrates an electrical barrier which has a plateau of constant height.

In a second embodiment, the plateau of the electric counter-field barrier is flat without increasing height of the plateau as shown in FIG. 3B, but the gas flow (53), (54) decreases in velocity along z-axis, for instance, by a gas flow in a tube widening in diameter along z, as shown in FIG. 3A. The effect is very similar to the effect by a plateau of increasing height. There may be even combinations between increasing plateau height and tube widening.

For an ion mobility spectrometer with this slightly increasing plateau or decreasing gas velocity, the optimum acquisition method decreases the field strength, $E_z$, of the electric barrier with $E_z(t)=c/t$ where c is a constant and t is time. This scan function not only generates ion mobility spectra with highest ion mobility resolution at moderate scan speed, but also generates a linear mobility scale.

The improvement of resolution with moderate acquisition speeds is based on the fact that now ions of a given mobility have longer to reside in the critical (and most selective) equilibrium state between being pulled forwards along the plateau by gas friction and being dragged back by the electric field. During this process of passing the plateau, the acquisition continues to decrease the height of the barrier, but due to the spatial gradient of the barrier's height (or due to the decreasing velocity of the gas), the ions are kept within this critical balance for some milliseconds, homogenizing the statistical Brownian movements of the ions caused by their Boltzmann energy distribution. The ions even may be less affected by space charge phenomena. For each gradient of the plateau, there exists an optimum of the acquisition speed for highest resolution. Once the optimum scan speed is chosen, a hyperbolic scan $E_z(t)=c/t$ automatically keeps this optimum, because the gradient of the plateau decreases proportionally with E. This hyperbolic scan $E_z(t)=c/t$, therefore, can be regarded as an optimum scan for the acquisition of mobility spectra with these devices. Besides, this scan results in a linear mobility scale of the mobility spectrum.

An exact mathematical investigation may even reveal that, for this type of spectrum acquisition, a slightly non-linear spatial gradient of the plateau might even be the optimum for highest resolution.

In total, the invention provides modifications of ion mobility devices for achieving highest resolution with moderate scan speeds. With application of these modifications and corresponding optimum acquisition methods, ion mobility spectra with resolutions by far exceeding $R_{mob}$=100 are to be expected, with mobility spectra on a linear mobility scale, and the resolution being almost constant along the ion mobility spectrum.

What is claimed is:

1. An ion mobility spectrometer having an axis and comprising:
    an electric field generator that generates an electric field barrier having a relatively steep ascent and a plateau with a height that increases slightly along the axis; and
    an ion source that entrains ions in a gas that flows along the spectrometer axis such that the gas blows the ions against and over the electric field barrier.

2. The ion mobility spectrometer of claim 1, wherein the plateau of the electric field barrier is curved along the axis.

3. The ion mobility spectrometer of claim 1, wherein the electric field generator comprises a network of resistors that generates a DC electric field barrier.

4. The ion mobility spectrometer of claim 1, wherein the electric field generator comprises an electrode configuration and an RF voltage generator that supplies RF voltages to the electrode configuration to generate an RF pseudofield field barrier produced by gradients of pseudopotentials at the electrode configuration.

5. The ion mobility spectrometer of claim 1, wherein the gas and the electric field barrier are enclosed by an RF multipole field.

6. The ion mobility spectrometer of claim 5, wherein the RF multipole field is generated inside a stacked ring ion guide.

7. The ion mobility spectrometer of claim 5, wherein the RF multipole field is generated inside a multipole rod system.

8. The ion mobility spectrometer of claim 7, wherein the RF multipole field is generated inside a quadrupole rod system.

9. The ion mobility spectrometer of claim 1, wherein the gas flow has a parabolic velocity profile normal to the axis and the electric field generator generates an electric field barrier with equipotential surfaces that are convex to the gas flow so that, for ions away from the axis, a lower gas flow velocity is compensated by the convexity of the equipotential surfaces.

10. The ion mobility spectrometer of claim 1, wherein the gas flow has a constant gas velocity along the axis.

11. An ion mobility spectrometer having an axis and comprising:
- an electric field generator that generates an electric field barrier having a plateau with a height that is constant along the axis; and
- an ion source that entrains ions in a gas that flows along the spectrometer axis such that the gas blows the ions against and over the electric field barrier, wherein the gas flow velocity decreases along the axis at the location of the plateau.

* * * * *